United States Patent [19]

Nyboer

[11] Patent Number: 4,787,599
[45] Date of Patent: Nov. 29, 1988

[54] SLIDE VALVE

[76] Inventor: Robert P. Nyboer, 819 W. Wilshire Blvd., Fullerton, Calif. 92632

[21] Appl. No.: 152,236

[22] Filed: Feb. 4, 1988

[51] Int. Cl.$^4$ .................................................. F16K 3/00
[52] U.S. Cl. .................................... 251/148; 251/326; 433/88; 604/902
[58] Field of Search .................. 251/326, 148; 433/88; 604/33, 118, 119, 902

[56] References Cited

U.S. PATENT DOCUMENTS

| | | | |
|---|---|---|---|
| 2,696,049 | 12/1954 | Black | 433/88 |
| 3,645,497 | 2/1972 | Nyboer | 604/902 |
| 4,430,073 | 2/1984 | Bemis et al. | 604/902 |

*Primary Examiner*—A. Michael Chambers
*Attorney, Agent, or Firm*—William C. Babcock

[57] ABSTRACT

An improved manually operated slide valve, particularly adept for use with a dental aspirator assembly, which valve is characterized by being formed from a number of components removably associated with one another to permit the valve to be disassembled for cleaning purposes. The improved value is also characterized by including means for preventing the slide member to move from an open to a closed position due to variations in pressure within the interior of the valve.

5 Claims, 1 Drawing Sheet

SLIDE VALVE

DESCRIPTION OF THE PRIOR ART

The slide valve of the present application is an improvement on the valve disclosed and claimed in my prior U.S. Pat. No. 3,645,497 entitled "Valve Structure" that issued on Feb. 29, 1972.

A major object of the present invention is to provide a slide valve that not only has the operational advantages of my previously patented valve, but has the additional advantages that it is formed from a number of components that are removably connected to one another, and may be easily disassembled for cleansing purposes which is highly desirable in the dental field.

A further object of the present invention is to supply a valve that overcomes an operational deficiency of my prior valve, namely, a tendency of the slide member to move inadvertently from an open to a closed position when there is a sudden change of negative pressure within the valve, such as occasioned by the aspirator assembly becoming clogged with tissue from a patient's mouth.

These and other objects and advantages of the improved slide valve will become apparent from the following description thereof and the drawing illustrating the improved slide valve.

SUMMARY OF THE INVENTION

An improved slide valve in which the valve body is defined by first and second valve body components having first and second longitudinal bores therein, with the first component slidably and removably engaging the second component. The first and second components when so engaged define a valve body that has an arcuate slot therein at the function of the first and second bores, and this slot movably supporting an elongate longitudinally extending flexible slide member which when in a first position obstructs communication between the first and second bores and when in a second position allows communication between the first and second bores.

The first valve component removably supports a tubular dental aspirator assembly that is in communication with the first bore. The second valve component is removably connected to a resilient tube that is in communication with a source of negative pressure. In addition, the first component includes means for preventing the inadvertent movement of the slide members from the second to the first position should there be a sudden increase in the negative pressure with the valve body, such as occurs if the aspirator assembly becomes temporarily clogged. Due to the above described structure the improved slide valve may be easily and quickly disassembled for cleansing purposes.

DESCRIPTION OF THE PREFERRED EMBODIMENT

Figure 1:
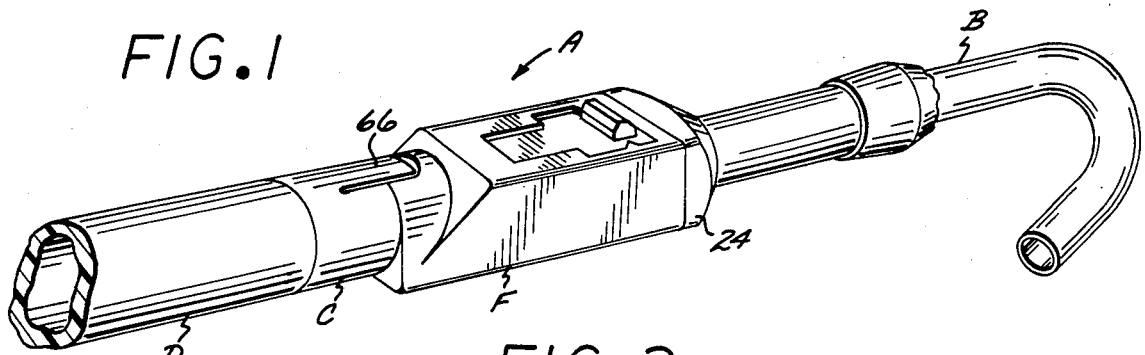
FIG. 1 is a perspective view of the improved slide valve in combination with a dental aspirator assembly.

The improved slide valve A of the present invention is shown in FIG. 1 as supporting a conventional dental aspirator B, with the slide valve being connected by a coupling C to a resilient tube D that leads to a negative source of pressure (not shown).

Figure 2:
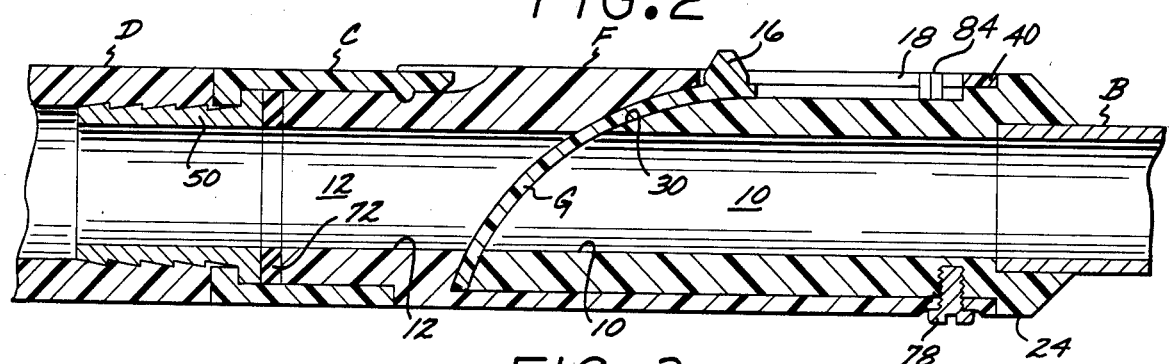
FIG. 2 is a longitudinal cross-sectional view of the slide valve with the slide valve member in a first position.
Figure 3:
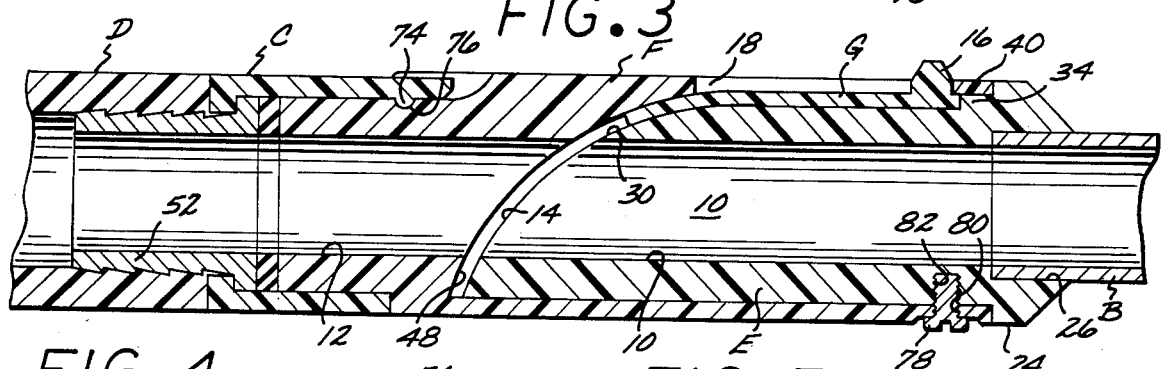
FIG. 3 is the same view shown in FIG. 2 but with the slide valve member in a second position.

The valve is defined by a first valve body component E that slidably and removably engages a second valve body component F best seen in FIG. 3. The first and second valve body components E and F have first and second longitudinal bores 10 and 12 therein that are axially aligned when the first and second components are in engagement as shown in FIGS. 2 and 3. When the first and second valve body components E and F are in engagement they cooperate to define a longitudinally extending arcuate slot 14 in which a slide member G is movably supported. The slide member G includes a finger engageable lug 16 that extends upwardly through an elongate opening 18 defined in second valve body component F shown in FIG. 6. The lug 16 may be used to manually move the slide member G to either the first position shown in FIG. 2 where communication between the first and second bores 10 and 12 is obstructed or to the second position illustrated in FIG. 3 where the first and second bores are in communication with one another, as well as to an intermediate position between the first and second positions.

Figure 6:
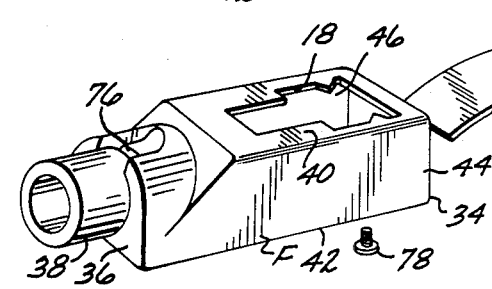
FIG. 6 is an exploded perspective view of the valve components.

The first valve body component E is of elongate shape as may be seen in FIG. 6 and has parallel side sufaces 20 and a bottom surface 22. First valve body component E has a first end 24 of enlarged transverse cross section in which a recess 26 is defined that is frictionally engaged by the tubular aspirator assembly B as shown in FIGS. 2 and 3.

First valve body component E has a second end 28 from which a convex elongate surface 30 extends forwardly to develop into a flat section 32 that terminates in a transverse stop 34 situated rearwardly of first end 24.

Second valve body component F as best seen in FIG. 6 has a first end 34 and a second end 36 from which a tubular member 38 projects that is in communication with second bore 12. The second valve body component F includes a top wall 40, bottom wall 42, and pair of side walls 44 that cooperate to define an elongate cavity 46 in which the first valve body component E is sealingly and removably disposed. The portion of the cavity 46 most adjacent the second end 36 of second valve body component F is defined by a concave surface 48 which in combination with a convex surface 30 define the arcuate slot 14. Opening 18 is defined in top wall 40 as shown in FIG. 6.

Figure 4:
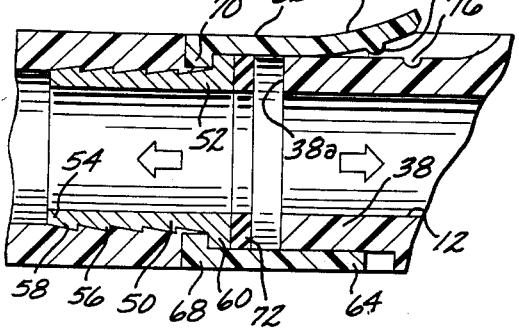
FIG. 4 is a fragmentary longitudinal cross-sectional view of the valve and a coupling assembly for removably connecting it to a resilient tube.

The coupling C is illustrated as including a rigid tube 50 that has a first end 52 and second end 54, and serrations 56 on the exterior thereof that frictionally engage the interior surface 58 of resilient tube D as shown in FIG. 4. An outwardly extending flange 60 is defined on first end 52. Coupling C further includes a cylindrical sleeve 62 that slidably and sealingly engages tubular member 38. The sleeve 62 has a first end portion 64 on which a tongue 66 is defined, and a second end 68 that has a circular rib 70 extending inwardly therefrom. The rib 70 is shown in FIG. 4 as in abutting contact with flange 60. A resilient washer 72 is disposed between flange 60 and the flat end surface 38a of tubular member 38. When the sleeve 62 is moved inwardly on tubular member 38 to the extent that a lug 74 on tongue 66 can engage a recess 76 on second valve body component F, the washer 72 is compressed between flange 60 and end surface 38a to effect a seal therewith.

The first and second valve body components E and F are illustrated as being removably held together by a screw 78 that extends upwardly through an opening 80 in bottom wall 42 to engage a tapped cavity 82 in first valve body component E.

The components above described may all be formed from a suitable commercially available polymerized resin.

Figure 5:
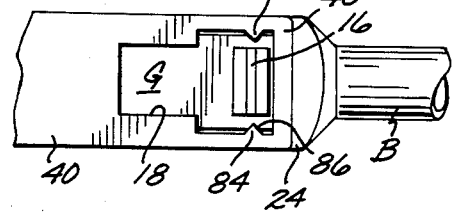
FIG. 5 is a top plan view of the slide valve illustrating the means employed to prevent inadvertent movement of the slide member from a second to a first position.

The slide member G is removably held in the second position by protuberances 84 that extend into opening 18 and engage notches 86 defined on the slide member as may be seen in FIG. 5. Although the first and second valve body components E and F are illustrated as being held together by a screw 78. Other means may be employed such as lug supporting tongues 66 that extend from one valve body component to engage recesses 76 formed in the other of the valve body components.

The structure of the improved slide valve A has been described previously in detail as well as the operation thereof and this information accordingly need not be repeated.

I claim:

1. A manually operated slide valve capable of being intermediately and removably disposed between a tubular aspirator assembly and a resilient tube in communication with a source of negative pressure, said valve characterized by being defined by a plurality of components that are removably connected to one another and may be separated for cleansing purposes, said valve including:
    a. a first valve body component that includes a first elongate body of non-circular transverse cross section that has first and second ends, with a first portion of said first body adjacent said first end of greater transverse cross section than the balance of said first body, said first body having an elongate convex surface thereon of substantial width that extends longitudinally from said second end towards said first portion, and a first bore that extends longitudinally through said first body;
    b. a second valve body component that includes a second elongate body that has first and second ends and a flat upper surface in which an elongate longitudinal opening is defined that is in communication with a cavity in said second body that extends longitudinally from said first end thereof towards said second end of said second body, a tubular member that extends from said second end of said second body and is in communication with a second bore in said second body that extends towards said first end thereof and a transverse concave surface defined in said second body at the junction of said second bore and cavity, said cavity of such transverse cross section as to sealingly engage said first body when the latter is disposed therein, and said first body of such length that when said first portion of said first body is in abutting contact with said first end of said second body a transverse arcuate slot is defined between said convex and concave surfaces;
    c. first means for removably holding said first and second valve body components together to define a valve body;
    d. an elongate resilient slide member longitudinally movable in said slot and extending under said longitudinal opening, said slide member when in a first position blocking communication between said first and second bores, and said slide member when in a second position establishing communication between said first and second bores;
    e. second means for moving said slide member between said first and second positions;
    f. third means for maintaining said slide member in said second position until such time as said slide member is moved manually to said first position by said second means;
    g. fourth means for removably supporting said tubular aspirator assembly from said first end portion of said first body and in communication with said first bore; and
    h. fifth means for removably securing said resilient tube to said tubular member.

2. A slide valve as defined in claim 1 in which said second means is a finger engageable lug that extends upwardly from said slide member through said opening.

3. A slide valve as defined in claim 1 in which said third means is at least one protuberance that extends from said second body into said opening and removably engages a notch in said slide member when said slide member is in said second position.

4. A slide valve as defined in claim 1 in which said fourth means is a recess in said first end portion that is frictionally engaged by said tubular aspirator assembly.

5. A slide valve as defined in claim 1 in which said fifth means comprises:
    i. a rigid tube that has first and second ends and a serrated exterior surface that sealing engages the interior of said resilient tube, and a flange that extends outwardly from said first end of said tube;
    j. a resilient cylindrical sleeve slidably and sealingly mounted on said tubular member, said sleeve having first and second ends, a circular rib that extends inwardly from said second end of said sleeve to engage said flange, a tongue that extends from said first end of said sleeve towards said first end of said second valve body, and a lug on said tongue; and
    k. a resilient washer in said sleeve that is in abutting sealing contact with said flange and end of said tubular member when said sleeve is moved longitudinally on said tubular member to a position where said lug on said tongue removably engages a recess in said second body.

* * * * *